United States Patent [19]
Contarini

[11] Patent Number: 5,222,508
[45] Date of Patent: Jun. 29, 1993

[54] METHOD FOR SUTURING PUNCTURES OF THE HUMAN BODY

[76] Inventor: Osvaldo Contarini, 6320 Wood Valley Rd., Jacksonville, Fla. 32217

[21] Appl. No.: 958,936
[22] Filed: Oct. 9, 1992
[51] Int. Cl.⁵ ............................................. A61B 19/00
[52] U.S. Cl. .................................... 128/898; 606/139
[58] Field of Search ............... 606/139, 144, 145, 146, 606/147, 215, 216

[56] References Cited

U.S. PATENT DOCUMENTS

| | | | |
|---|---|---|---|
| 4,526,173 | 7/1985 | Sheehan | 606/216 |
| 5,009,663 | 4/1991 | Broomé | 606/215 |
| 5,037,433 | 8/1991 | Wilk et al. | 606/139 |

Primary Examiner—Stephen C. Pellegrino
Assistant Examiner—Gary Jackson
Attorney, Agent, or Firm—Thomas C. Saitta

[57] ABSTRACT

A method for suturing puncture wounds in the human body, such as those made by surgical trocars, comprising the steps of providing insertion means and retrieval means for suturing material, inserting the insertion means and suture through the internal tissue layers adjacent to the puncture, inserting the retrieval means through the internal tissue layers, retrieving the suture, withdrawing the insertion means, retrieval means and suture, and then tightening and tieing the suture to close the puncture wound internally.

7 Claims, 1 Drawing Sheet

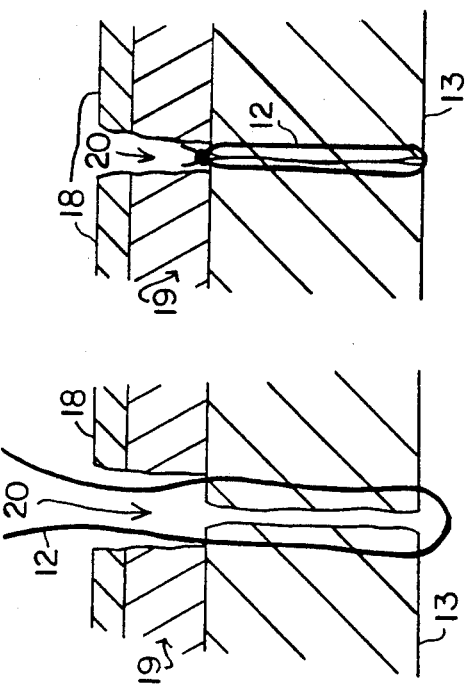
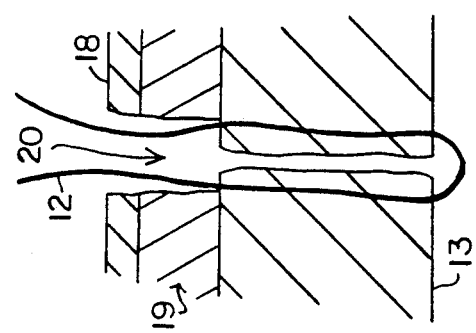
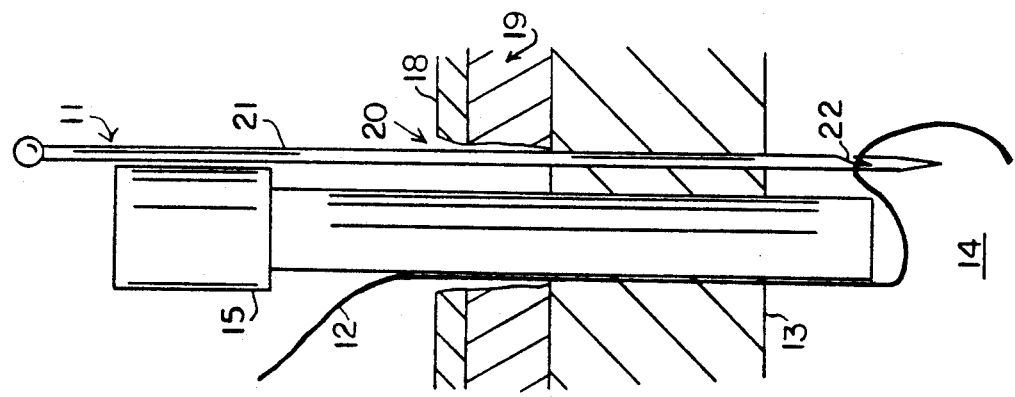
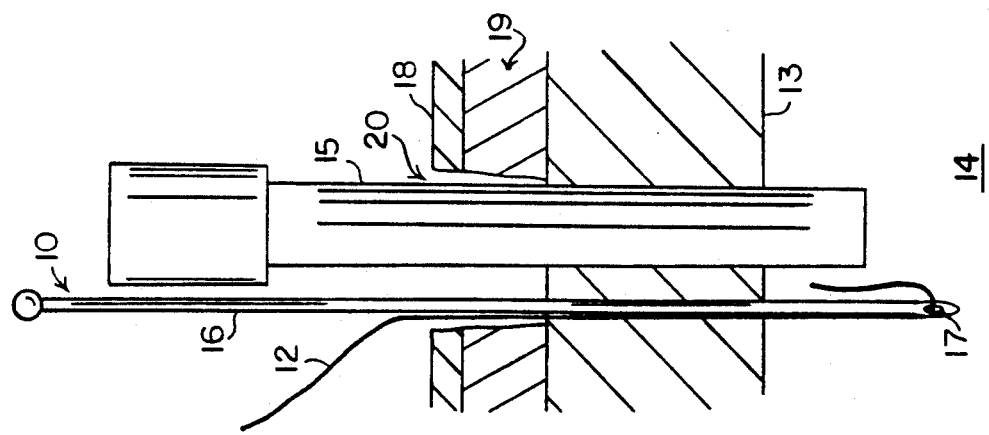

METHOD FOR SUTURING PUNCTURES OF THE HUMAN BODY

BACKGROUND OF THE INVENTION

This invention relates generally to methods for closing punctures and small wounds of the human body, such as those made by surgical trocars for performing endoscopic or thoracoscopic surgery. More particularly, the invention relates to a novel suturing method which allows such punctures to be sutured and closed with an internal seal on the puncture.

Many recent surgical techniques involve the use of trocar devices to create access to specific internal areas of the human body. Rather than requiring a relatively large incision to provide access for the surgeon, the new tools developed for endoscopic and thoracoscopic surgery allow work to be performed via entry through only a small opening in the body wall. In general, the trocar and its sleeve assembly are used to puncture the patient's skin, subcutaneous tissue, and internal tissue layers (muscles, fascia and peritoneum or pleura, for example) to provide access to an internal body cavity or area. After removal of the piercing trocar, the necessary procedures are implemented by introducing the surgical tools through valving mechanisms in the sleeve device.

Upon completion of the procedure, the sleeve is removed, leaving a puncture opening which must now be sealed. Traditional technique is to close the opening by suturing the outermost layers of skin and subcutaneous tissue. The interior portion of the puncture is not addressed, and usually the muscles and fascia will seal the defect in due course. In some cases, the surgeon will attempt to suture the opening within the muscle and fascia layer, utilizing standard curved suturing needles. This is extremely difficult to accomplish due to the small size of the opening, usually 5 to 12 millimeters, and the task is further impeded by the overall length of the puncture, which can be of some distance for overweight patients. Use of a large curved needle makes recovery almost impossible after transfixing one side of the defect and a small needle will not sufficiently pass through the entire internal muscle-fascia tissue layer for proper suturing.

Without closure of the puncture defect from the interior, complications such as excessive bleeding, hernia formation, bowel strangulation or fluid migration into the internal tissue layers may occur. To solve this problem, a novel and unique technique has been developed for internal closure of small wounds and trocar punctures, whereby the internal tissue layers are sutured shut to seal the puncture defect internally as well as externally.

It is an object of this invention to provide a method for internally closing puncture openings in the human body, such as are created by surgical trocar devices, whereby the defect is sealed across the interior of the puncture by suturing.

It is a further object to provide such a method whereby the suturing material can be positioned prior to removal of the trocar sleeve, such that the closure can be accomplished immediately following removal of the trocar sleeve.

It is a further object to provide such a method whereby the puncture defect in the internal tissue layer can be closed by one or several sutures introduced through the skin opening of the puncture itself and passed through the internal layers, such that the sutures can be quickly tightened to seal the internal tissue layers and tied below the skin surface within the subcutaneous layer.

SUMMARY OF THE INVENTION

The method is directed at providing a technique for internally sealing puncture defects in the human body, such as may occur in wounds or through the use of surgical trocars. The method is suitable for punctures of small diameter. For example, trocar punctures are typically of the magnitude of only 5 to 12 millimeters in diameter, making it very difficult or impossible to apply traditional suturing techniques within the internal layers. The method provides a technique for quickly and easily suturing the defect within the internal tissue layers (e.g., muscle-fascia-peritoneum for abdominal cases and muscle-fascia-pleura for thoracic cases), whereby the defect is closed across the point of entry to an internal body cavity with the aid of endoscopy, in addition to being closed externally.

The method comprises the initial step of providing suture insertion means and suture retrieval means, the means generally comprising needles of suitable length having apertures or barbs for control and manipulation of the suture material. The suture is threaded or attached to the insertion needle, which is then inserted through the internal tissue layers adjacent to the puncture defect and trocar sleeve until the free end of the suture material is positioned within the internal body cavity. The retrieval needle is then inserted through the internal tissue layers adjacent to the puncture and trocar sleeve but opposite from the initial insertion. The suture is then snared or hooked by the retrieval needle, which act may be aided by the use of grasping forceps where necessary. Both the insertion needle and retrieval needle with suture are then withdrawn through the internal tissue layers. This technique results in the suture material being positioned across the puncture opening within the body cavity, with both free ends of the suture material now external to the internal tissue layers within the subcutaneous layer. If necessary, a second pass with the same suture or a separate suture is made using the same steps to create a more effective closure across the internal opening. After removal of the trocar sleeve, the exposed ends of the sutures are then drawn tight, closing the puncture within the internal tissue layers at both the interior and exterior entry points. The suture is then tied within the subcutaneous layer. The external skin layer is then sutured closed using traditional techniques.

BRIEF DESCRIPTION OF THE DRAWINGS

FIG. 1 illustrates the insertion needle and suture upon completion of the step of inserting the suture material through the internal body layers.

FIG. 2 illustrates the retrieval needle and suture after the steps of snaring the suture and removing the insertion needle.

FIG. 3 illustrates the positioning of the suture material after the steps of withdrawal of the trocar sleeve and retrieval needle.

FIG. 4 illustrates the sealed puncture defect after the step of tieing the suture material.

DETAILED DESCRIPTION OF THE INVENTION

The invention is a method for sealing small diameter wounds or punctures in the human body, where the minimal size of the puncture and the thickness of the body tissue layers prevent the use of traditional suturing techniques for the internal portion of the puncture. For purposes of this disclosure, the method will be disclosed with reference to a puncture wound made by a surgical trocar. Such punctures are typically in the range of 5 to 12 millimeters in diameter. The depth of the puncture is a function of the thickness of the tissue layers comprising the external skin layer, the subcutaneous layer and internal tissue layers into an internal body cavity such as the abdomen or chest. By internal tissue layers, it shall be taken to mean layers interior to the subcutaneous layer, such as for example the muscle-fascia-peritoneum layers of the abdomen or the muscle-fascia-pleura layers of the chest.

In general, the method comprises the initial step of providing insertion means 10 for introduction of a suture material 12 through the internal tissue layers 13 and into the internal cavity 14 and separate retrieval means 11 for withdrawal of the suture material 12 from the internal cavity 14 through the internal tissue layers 13. The insertion means 10 includes any device capable of passing the suture material 12 through the internal tissue layers 13, such as a long needle 16 having means for temporary connection of the suture material 12 at or near the piercing end of this insertion needle 16. As shown in FIG. 1, the insertion needle 16 may have an eyelet 17 through which is threaded the suture material 12. Alternatively, the insertion needle 16 may have a slot or barb to retain the suture material 12 during insertion. The insertion means 10 and the retrieval means 11 are preferably constructed of stainless steel, although any similar material having suitable characteristics may also be used, and they may be curved or straight.

The suture material 12 is connected to the insertion needle 16 and the internal tissue layers 13 are pierced by positioning the insertion needle 16 within the puncture opening 20 in the skin layer 18 and subcutaneous layer 19. The insertion needle 16 is pushed completely through the internal tissue layers 13 adjacent to the puncture 20 and trocar 15, such that one free end of the suture material 12 extends through into the internal cavity 14. Upon completion of this step, the positioning of the insertion needle 16 and suture material 12 relative to the puncture 20 and trocar 15 is as shown in FIG. 1.

Retrieval means 11 is now inserted through the internal tissue layers 13 to retrieve the free end of the suture material 12. Retrieval means 11 may include any device capable of piercing the internal tissue layers 13 and retrieving the suture material 12 from the internal cavity. As shown in FIG. 2, retrieval means 11 may comprise a retrieval needle 21 having a barbed or slotted portion 22 for retention of the suture material 12 during withdrawal. Retrieval means 11 could alternatively comprise a manipulatable snaring or looped device.

The retrieval needle 21 is inserted through the internal tissue layers 13 via the puncture opening 20 in the subcutaneous layer 19. The insertion is made adjacent the puncture 20 and trocar 15 at a point opposite that of the insertion point of the insertion needle 16 and sufficiently deep so that the barbed portion 22 exits the internal tissue layers 13 into the internal cavity 14. The free end of the suture material 12 inside the internal cavity 14 is grasped or snared by the barbed portion 22 of the retrieval needle 21. If necessary, this connection of the suture material 12 to the retrieval needle 21 may be accomplished with the aid of grasping forceps. The insertion needle 16 is then withdrawn, resulting in the situation as shown in FIG. 2.

With the retrieval needle 21 withdrawn, the free end of the suture material 12 is now external to the puncture 20. If desired, the above steps may now be repeated using the same suture material 12 or a separate suture material 12, such that the suture material 12 is again inserted by the insertion needle 16 through the internal tissue layers 13 and again retrieved by the retrieval needle 21. Preferably, the points of entry and exit for the suture material 12 within the internal cavity 14 are either parallel to the line between the original points of entry and exit for the first suture 12 or are on opposite sides of this original line to form an "X".

Upon removal of the trocar 15 from the puncture 20, the situation shown in FIG. 3 is achieved. The suture material 12 now runs in one or several continuous strands paralleling the puncture 20 and crossing the opening within the internal cavity 14. The suture material 12 is then tightened to draw the internal tissue layers 13 together to seal the puncture 20, as shown in FIG. 4. Because the suture material 12 crosses the internal opening of the puncture 20, the puncture 20 is sealed and closed at the internal cavity 14 and, upon tieing, at the external opening of the puncture 20 on the exterior side of the internal tissue layers 13. The remaining opening in the subcutaneous layer 19 and skin layer 18 can then be closed with standard suturing techniques.

Since the suture material 12 is drawn tight across the internal opening of the puncture 20, the puncture is effectively and completely sealed at both ends. Closure of the internal portion of the puncture 20 is not left to natural body healing processes, and the potential problems of bleeding, fluid leakage, hernia formation or bowel obstruction are obviated.

The above examples are by way of illustration only, and it is envisioned that those skilled in the art may surmise obvious equivalents and substitutions for the steps described above. The full scope and definition of the invention therefore is to be as set forth in the following claims.

I claim:

1. A method for suturing puncture wounds of the human body which extend through the skin layer, subcutaneous layer, internal tissue layers, and into an internal body cavity, comprising the steps of:
   (A) providing suture material having at least one free end, insertion means for inserting said suture material through said internal tissue layers and into said internal cavity, and retrieval means for withdrawing said suture material from said internal cavity and through said internal tissue layers;
   (B) temporarily connecting said suture material to said insertion means;
   (C) inserting said insertion means and said suture material through said internal tissue layers adjacent to said puncture wound, whereby said free end of said suture material is inserted into said internal cavity;
   (D) inserting said retrieval means through said internal tissue layers adjacent to said puncture wound and into said internal cavity;
   (E) temporarily connecting said free end of said suture material within said internal cavity to said retrieval means;
   (F) withdrawing said insertion means from said internal cavity;

(G) withdrawing said retrieval means and said free end of said suture material from said internal cavity through said internal tissue layers;

(H) tightening said suture material whereby said puncture wound is closed by said suture material within said internal cavity and external to said internal tissue layers.

2. The method of claim 1, further comprising the steps of reconnecting said free end of said suture material to said insertion means prior to said tightening and closure of said puncture wound; again inserting said insertion means and free end of said suture material through said internal tissue layers adjacent said puncture wound, whereby said free end of said suture material is inserted into said internal cavity; again inserting said retrieval means through said internal tissue layers adjacent to said puncture wound and into said internal cavity; again temporarily connecting said free end of said suture material within said internal cavity to said retrieval means; again withdrawing said insertion means from said internal cavity; and again withdrawing said retrieval means and said free end of said suture material from said internal cavity through said internal tissue layers.

3. The method of claim 1, where said insertion means comprise a needle and said retrieval means comprise a needle.

4. The method of claim 3, where said insertion needle comprises an eyelet and said step of connecting said suture material to said insertion means comprises threading said suture material through said eyelet.

5. The method of claim 3, where said retrieval needle comprises a barbed portion and said step of connecting said suture material to said retrieval means comprises connecting said suture material to said barbed portion.

6. The method of claim 1, where said steps of inserting said insertion means and said retrieval means further comprises inserting said insertion means and retrieval means through said puncture wound itself in said skin and subcutaneous layers.

7. The method of claim 1, further comprising the step of closing said puncture wound in said subcutaneous and skin layers by suturing.

* * * * *